United States Patent
Yoshioka et al.

(10) Patent No.: US 11,926,927 B2
(45) Date of Patent: Mar. 12, 2024

(54) METHOD OF COLLECTING BAGWORM SILK THREAD

(71) Applicants: NATIONAL AGRICULTURE AND FOOD RESEARCH ORGANIZATION, Tsukuba (JP); KOWA COMPANY, LTD., Nagoya (JP)

(72) Inventors: Taiyo Yoshioka, Tsukuba (JP); Tsunenori Kameda, Tsukuba (JP); Akimune Asanuma, Tsukuba (JP); Hironori Sassa, Tsukuba (JP)

(73) Assignees: NATIONAL AGRICULTURE AND FOOD RESEARCH ORGANIZATION, Tsukuba (JP); KOWA COMPANY, LTD., Nagoya (JP)

( * ) Notice: Subject to any disclaimer, the term of this patent is extended or adjusted under 35 U.S.C. 154(b) by 931 days.

(21) Appl. No.: 16/957,990

(22) PCT Filed: Dec. 18, 2018

(86) PCT No.: PCT/JP2018/046597
§ 371 (c)(1),
(2) Date: Jun. 25, 2020

(87) PCT Pub. No.: WO2019/131333
PCT Pub. Date: Jul. 4, 2019

(65) Prior Publication Data
US 2021/0372007 A1    Dec. 2, 2021

(30) Foreign Application Priority Data

Dec. 27, 2017   (JP) .................................. 2017-251904

(51) Int. Cl.
*D01B 7/00*     (2006.01)
*A01K 67/04*    (2006.01)
(Continued)

(52) U.S. Cl.
CPC ................. *D01B 7/06* (2013.01); *A01K 67/04* (2013.01); *D01C 3/02* (2013.01)

(58) Field of Classification Search
CPC ............. D01B 7/06; A01K 67/04; D01C 3/02
(Continued)

(56) References Cited

U.S. PATENT DOCUMENTS

| 3,465,720 A | * | 9/1969 | Masaki | A01K 67/04 |
| | | | | 119/270 |
| 3,994,259 A | * | 11/1976 | Sakamura | A01K 67/04 |
| | | | | 119/270 |
| 2015/0176157 A1 | * | 6/2015 | Liu | D01B 7/00 |
| | | | | 119/270 |

FOREIGN PATENT DOCUMENTS

| JP | H03220119 A | 9/1991 |
| JP | H04276403 A | 10/1992 |
| JP | H1036548 A | 2/1998 |
| JP | 2001190384 A | 7/2001 |
| WO | 2012165477 A1 | 12/2012 |

OTHER PUBLICATIONS

Reddy et al., "Structure and properties of ultrafine silk fibers produced by Theriodopteryx ephemeraeformis", J Mater Sci, 2010, vol. 45, No. 24, pp. 6617-6622.
(Continued)

*Primary Examiner* — Richard T Price, Jr.
(74) *Attorney, Agent, or Firm* — Lucas & Mercanti, LLP

(57) ABSTRACT

Developed and provided is a method of collecting a large amount of high-quality bagworm silk threads having no contaminant from bagworm nests in a convenient manner and at low cost. The habit of bagworms is utilized to allow a bagworm to build a nest using solvent-soluble substances
(Continued)

or thermally meltable substances as nest materials, followed by dissolving or melting the nest materials to separate the nest material from the bagworm silk threads, whereby only pure bagworm silk threads constituting the bagworm nest can be obtained.

11 Claims, 6 Drawing Sheets

(51) Int. Cl.
*D01B 7/06* (2006.01)
*D01C 3/02* (2006.01)
(58) Field of Classification Search
USPC .......................................................... 119/270
See application file for complete search history.

(56) References Cited

OTHER PUBLICATIONS

Supplementary European Search Report for Corresponding European Application No. 18895308.7, daed Aug. 30, 2021, 4 pages.
Osaki., "Animals Teach Science on Natural Fibers:- Spider's Silks, Bagworm's Silks, and Collagen Fibers-", Journal of the Society of Fiber Science and Technology, 2002, vol. 58, No. 3, pp. 74-78., English translation 3 pages.
Gosline et al., "The Mechanical Design of Spider Silks: From Fibroin Sequence to Mechanical Function", The Journal of Experimental Biology, 1999, vol. 202, pp. 3295-3303.
International Search Report for Corresponding Application No. PCT/JP2018/046597 ( 2 Pages) (dated Apr. 2, 2019).

* cited by examiner a b c d e

METHOD OF COLLECTING BAGWORM SILK THREAD

CROSS-REFERENCE TO RELATED APPLICATIONS

This application is a 371 of PCT/JP2018/046597, filed Dec. 18, 2018, which claims the benefit of Japanese Patent Application No. 2017-251904, filed Dec. 27, 2017.

TECHNICAL FIELD

The present invention relates to a method of collecting silk thread derived from moth larva belonging to the family Psychidae, i.e., a bagworm, non-woven fabric obtained using the method thereof and nest material used in the method.

BACKGROUND ART

The thread consisting of an insect cocoon or a hair of mammal has been used as an animal fiber for a cloth and the like since long time ago. Especially, silk thread from a silk moth (*Bombyx mori*) larva, namely a silkworm, which is herein often referred to as "silkworm silk thread", has excellent properties for absorption and desorption of moisture, moisture retention, and heat retention, and also has a unique gloss and a smooth texture. Therefore, the silkworm silk thread is valuable and expensive natural material even today.

However, there exist animal fibers in nature having properties comparable or superior to those of silkworm silk thread. Recently, for utilizing an animal fiber having such excellent properties as novel natural material, exploration thereof and research thereon is ongoing.

The larvae of moth belonging to the family Psychidae in the order Lepidoptera is collectively referred to as a bagworm (also known as "basket worm") and is known to spend the whole larval stages living with a spindle-shaped or cylinder-shaped nest (herein often referred to as a "bagworm nest") made of pieces of leaves and twigs assembled by thread, during which the larva usually hide itself inside the nest and move with the nest even for eating.

The silk thread spun by the bagworm (herein often referred to as "bagworm silk thread") has recently been attracting attention as a new animal-fibrous natural material having more excellent properties than the silkworm silk thread. For example, the bagworm silk thread from the bagworm *Eumeta minuscula* has an elastic modulus up to 3.5 times of that of the silkworm silk thread and a very high strength (Non-Patent Literatures 1 and 2). Additionally, the bagworm silk thread not only have a gloss and a shiny appearance comparable or superior to those of the silkworm silk thread but also allow production of much fine, thin and light fabric with a smooth texture compared to the silkworm silk thread because monofiber of the bagworm silk thread has a cross-sectional area only about one-seventh of that of the silkworm silk thread.

The bagworm is more advantageous than the silkworm also in terms of rearing. For example, since the silkworm feeds on only raw leaves of mulberry (species belonging to the genus *Morus*, including, for example, *M. bombycis*, *M. alba*, and *M. lhou*) in principle, the region for rearing and season for rearing depend on the supply area of mulberry leaves and the season of mulberry leaf development. In contrast, the bagworm is euryphagous, the specificity for food leaves is low, and many species of the bagworm can feed on leaves of trees of various species. Accordingly, food leaves for the bagworm are easily obtainable and the bagworm can be raised in any region. Also, the bagworm of some species can feed on leaves of evergreen trees. Thus, differently from mulberries, which are deciduous trees, it is possible to supply food leaves all year round. Moreover, the bagworm is smaller in size than the silkworm and requires a rearing space equal to or less than that required for rearing the silkworm, which makes mass rearing easy. Thus, the cost for rearing can significantly be reduced compared with that for rearing the silkworm.

Also, the bagworm is superior to the silkworm in terms of productivity. For example, the silkworm spins a large amount of threads only during cocooning and all larvae perform cocooning in the same period. Thus, thread collection periods overlap and labor periods concentrate thereon. However, the bagworms repeatedly spin silk thread for nest building or migration throughout larval stages. Thus, labor periods can be dispersed by artificially adjusting the thread collection periods.

As described above, the bagworm silk thread has properties superior to those of the silkworm silk thread and also has many advantages for their production, and thus, is expected as a very promising novel natural material.

However, for the practical application of bagworm, several problems have to be solved. One of them is a problem associated with the characteristics of the bagworm nest. Contaminants, such as pieces of leaves and twigs, are inevitably attached on the surface of the bagworm nest. This is due to the habit of the bagworm incorporating small pieces of twigs and leaves into the nests from the surroundings for camouflage in the process of nest production and expansion. These contaminants need to be completely removed for commercialization of the bagworm silk thread. In conventional method, these contaminants are manually removed from the built bagworm nest, or are detached after the bagworm nest being immersed in warm water for a long time to be softened. However, the work of removing these contaminants requires enormous labor. Additionally, complete removal of the contaminants is not possible with existing technologies, resulting in a problem in that only low quality final products can be obtained, due to contamination with a small amount of small pieces of leaves and the like, as well as light-brown staining of the silk thread with pigments from the contaminants and so on. A decolorization treatment can be carried out using a base or an acid to remove the pigments, but can result in a marked decrease in quality such as an impaired strength of the bagworm silk thread. It has been essential to solve the problems described above for practical application of the bagworm silk thread, but hitherto, there have been no convenient or inexpensive method of collecting pure and high-quality the bagworm silk thread comprising no contaminant and without a stain.

CITATION LIST

Patent Literature

Patent Literature 1: WO2012/165477

Non-Patent Literature

Non-Patent Literature 1: Shigeyosi Ohsaki, 2002, Sen'i Gakkaishi (Sen'i To Kogyo), 58: 74-78.

Non-Patent Literature 2: Gosline J. M. et al., 1999, 202, 3295-3303.

SUMMARY OF INVENTION

Technical Problem

An purpose of the present invention is to develop and provide a method of collecting a large amount of high-quality bagworm silk thread comprising no contaminant from bagworm nest in a convenient manner and at low cost. Another purpose is to allow such bagworm silk thread for practical application as a novel natural material.

Solution to Problem

A bagworm which has been taken out of a nest and made wholly uncovered (herein such a bagworm is often referred to as a "naked bagworm") will promptly move to a nest building action for self-protection and to keep itself warm. In this case, the bagworm habitually incorporates small pieces of materials into the bagworm nest from the bagworm's surrounding as alternative nest materials to leaves and twigs. In Japan, child's play making use of this habit is known since old time, i.e., making a colorful bagworm nest into which wool waste of various colors and small pieces of various colored paper have been incorporated.

To solve the problems described above, the present inventors have developed a novel method of collecting thread utilizing the habit of the bagworm. Provided with solvent-soluble substances or thermally meltable substances as nest materials, a naked bagworm builds a nest using them. Then, the newly produced bagworm nest is treated with solvent or heat depending on the nest materials mixing in the bagworm nest, whereby the nest materials can be dissolved or melted. Subsequently, the dissolved or melted nest materials being separated, only the bagworm silk thread constituting the bagworm nest can be obtained. The present invention provides the followings based on the method of collecting described above.

(1) A method of collecting a bagworm silk thread, comprising:
placing process of placing a naked bagworm separated from a bagworm nest, together with a nest material(s) soluble in a solvent which does not damage, denature, or dissolve the bagworm silk thread;
nest building process of allowing the naked bagworm to build a bagworm nest using the nest material(s);
dissolving process of dissolving the nest material(s) in the solvent; and
separation process of separating the dissolved nest material(s) from the bagworm silk thread.

(2) The method according to (1), further comprising collection process of collecting the bagworm nest after the nest building process and before the dissolving process.

(3) The method according to (1) or (2), wherein the solvent is water.

(4) The method according to (1) or (2), wherein the solvent is a low-polarity solvent.

(5) A method of collecting bagworm silk thread, comprising:
placing process of placing a naked bagworm separated from a bagworm nest, together with a thermally meltable nest material(s);
nest building process of allowing the naked bagworm to build a bagworm nest using the nest material(s);
melting process of melting the nest material(s) under heating at a temperature which does not damage, thermally denature, or melt the bagworm silk thread; and
separation process of separating the melted nest material from the bagworm silk thread.

(6) The method according to (5), further comprising collection process of collecting the bagworm nest after the nest building process and before the melting process.

(7) The method according to any one of (1) to (6), wherein the naked bagworm is placed in a recess of a plate in the placing process, the recess being containable the single naked bagworm body.

(8) The method according to (7), wherein the plate is light-blocking.

(9) The method according to any one of (1) to (8), further comprising a cleaning process of cleaning the separated bagworm silk thread.

(10) The method according to any one of (1) to (9), further comprising a drying process of drying the bagworm silk threads

(11) An unwoven fabric formed of the bagworm silk thread obtainable by using the method of collecting the bagworm silk thread according to any one of (1) to (10).

(12) A nest material for collecting a bagworm silk thread, wherein the nest material is water-soluble and has a thin and small piece of shape or rod shape having the maximum length of 40 mm or less.

(13) A nest material for collecting a bagworm silk thread, wherein the nest material is soluble in a low-polarity solvent and has a thin and small piece of shape or rod shape having the maximum length of 40 mm or less.

(14) A nest material for collecting a bagworm silk thread, wherein the nest material is thermally meltable and has a thin and small piece of shape or rod shape having the maximum length of 40 mm or less.

The present specification encompasses the contents disclosed in the specification and/or drawings of Japanese Patent Application No. 2017-251904, on which the priority of the present application is based.

Advantageous Effects of Invention

By the method of collecting according to the present invention, it is possible to collect a large amount of high-quality bagworm silk threads comprising no contaminant from bagworm nests in a convenient manner in a short time. This makes it possible to provide more inexpensive and higher-quality bagworm silk thread than conventional methods.

DESCRIPTION OF EMBODIMENTS

1. Definition of Terms

Figure 1A:
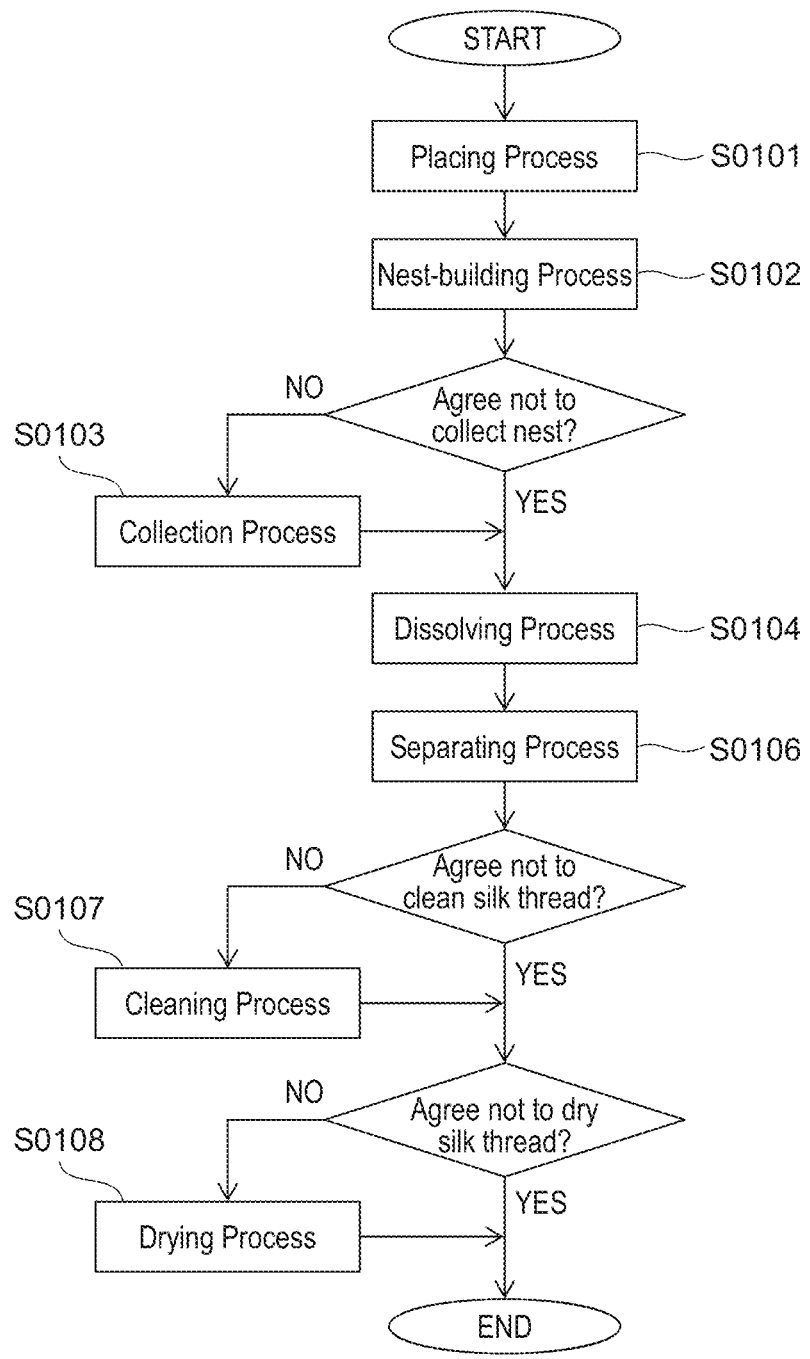
FIG. 1A shows a process flow diagram of a method of collecting a bagworm silk thread according to the present invention. This flow diagram shows a case in which the nest materials to be used are a solvent-soluble substance.

The following terms frequently used herein are defined as described below.

The term "bagworm" collectively refers to a moth larva belonging to the family Psychidae in the order Lepidoptera, as described above. Moths belonging to the family Psychidae are distributed worldwide and the larva (bagworm) of any species of the moth spends the whole larval stages living in a nest covered with natural materials, such as pieces of leaves and twigs, which are assembled by silk threads spun by the larva itself. Furthermore, any species of bagworm has the habit of building a nest using, in principle, nest materials in the surroundings when taken out of a nest. Accordingly, the species, instar, and gender of bagworms used herein are not limited, as long as that the bagworm is a larva of a moth species belonging to the family Psychidae and that the species has the habit as described above. For example, the family Psychidae includes the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, etc., and the bagworm used herein may be a species belonging to any genus. Additionally, the instar of the larva may be any instar between the first instar and the last instar. However, larger bagworm is preferable to obtain a large mass of the bagworm silk thread. For example, among larvae of the same species, larva in the last instar is more preferable, and female larva is more preferable than male larva because female grows larger than male. Furthermore, among the family Psychidae, large species is more preferable. For example, *Eumeta japonica* and *Eumeta minuscula*, which are large species, are suitable as species used in the present invention. As described above, a bagworm which has artificially been taken out of a nest and made wholly uncovered is often referred to as a "naked bagworm", as used herein. In principle, since a bagworm in nature never exposes its whole body out of a nest throughout the larval stage, a naked bagworm to be used herein for the purpose of nest building means an artificially prepared bagworm.

The term "silk thread" as used herein refers to a thread derived from an insect and made of proteins, which is spun by the insect in larval or adult stage for the purpose of nest building, migration, anchoring, cocooning, prey capture, and the like. When the term "silk thread" is simply recited herein, it refers to a general silk thread from unspecified insect. In case of indicating a silk thread from a particular insect species, the name of the organism is placed before the term "silk thread," as "silkworm silk threads" or "bagworm silk threads."

The term "bagworm silk thread" as used herein refers to silk threads spun by a bagworm. The "bagworm silk thread" herein encompasses monofiber, spun fiber, and fiber assembly.

The term "monofiber" as used herein, which is also referred to as monofilament, is the smallest filament unit constituting fiber components. The monofiber contains a fibroin protein as a main component. The bagworm silk thread and the silkworm silk thread in natural states are spun in the form of bifilament in which two monofibers are joined together by a sericin protein, a gummy material. This bifilament is referred to as a "spun fiber". The bagworm nest and the silkworm cocoon are constituted with spun fiber(s). Also, a fiber bundle formed by assembling plural spun fibers is referred to as a "fiber assembly (or multifilament)". Raw silk thread obtained after undergoing a silk reeling process is this multifilament. Furthermore, silk thread obtained by treatment of raw silk thread with an enzyme and a basic chemical such as soap, lye, sodium carbonate, and urea to remove sericin protein is called scoured silk thread.

The bagworm silk thread includes two kinds of the silk thread: foothold silk thread and nest silk thread. The "foothold silk thread" refers to silk thread spun by a bagworm for the purpose of its migration, which has a function as a scaffold for preventing it from falling from branch, leaf, or the like. A bagworm spins the foothold silk thread in the intended direction and in a zigzag pattern upon its migration, and the bagworm hooks its claws onto the foothold silk thread to move. On the other hand, the "nest silk thread" refers to the silk thread forming a nest, which is spun to assemble pieces of leaves and twigs or to make an internal wall of a nest so that its accommodation space becomes a comfortable environment. Accordingly, the bagworm silk thread to be subject to the invention in this specification is the nest silk thread, in principle. On this basis, the bagworm silk thread herein refers to the nest silk thread unless otherwise specified.

The term "bagworm nest (or bag nest)" as used herein refers to a spindle-shaped, cylinder-shaped, or dome-shaped nest made by a bagworm, and is constituted with the bagworm silk thread (nest silk thread) and the nest material. A method of collecting thread according to the present invention is a method of collecting bagworm silk thread constituting this bagworm nest.

The term "dome-shaped bagworm nest" used herein is a half-spindle-shaped bagworm nest looked like a usual spindle-shaped bagworm nest cut in parallel to its long axis.

The term "nest material" as used herein is a substance other than the bagworm silk thread, incorporating into a nest of a bagworm upon nest building. As described above, a bagworm usually wears plant leaves and small pieces of twigs on the surface of its nest for the purpose of camouflage or the like. In nature, these plant leaves and small pieces of twigs corresponds to the nest material. When a bagworm is forced into the state of a naked bagworm, the bagworm immediately rebuilds a bagworm nest using various substances in its surroundings as nest materials for self-protection and to keep itself warm. Accordingly, placing desired nest materials around a naked bagworm, any nest materials can be incorporated into the bagworm nest. The present invention is characterized in that specific materials with predetermined properties are used as these nest materials. In each aspect below, it is described about the nest material such as about its component, size, shape, and so on.

The term "solvent" as used herein refers to a solvent that does not damage, denature, or dissolve bagworm silk threads, particularly fibroin protein that is a fiber component of the thread. For example, none of a strong acidic solvent and a strong basic solvent that denature protein is suitable as a solvent to be used in the present invention. The solvents can be classified into high-polarity solvent (hydrophilic solvent) and low-polarity solvent (hydrophobic solvent) based on the degree of their polarity, and both solvents are encompassed herein. High-polarity solvent includes water and some organic solvents, such as lower alcohol (methanol, ethanol, etc.), and acetic acid. Also, low-polarity solvent includes many other organic solvents (low-polarity organic solvent), such as hexane, toluene, chloroform, dichloromethane, dichloroethane, trichloroethylene, acetone, diethyl ether, xylene, carbon tetrachloride, methyl acetate, ethyl acetate, tetrahydrofuran, acetonitrile. Considering the easiness of handling (including waste liquid disposal), safety, and purchasing cost, water (including warm water and hot water) is particularly preferable as a solvent in the present invention.

The term "solvent-soluble" used herein refers to the capability to dissolve in the specific solvents mentioned above. Accordingly, a "solvent-soluble nest material" refers to a nest material that can dissolve in a specific solvent.

2. Method of Collecting Threads

Figure 1B:
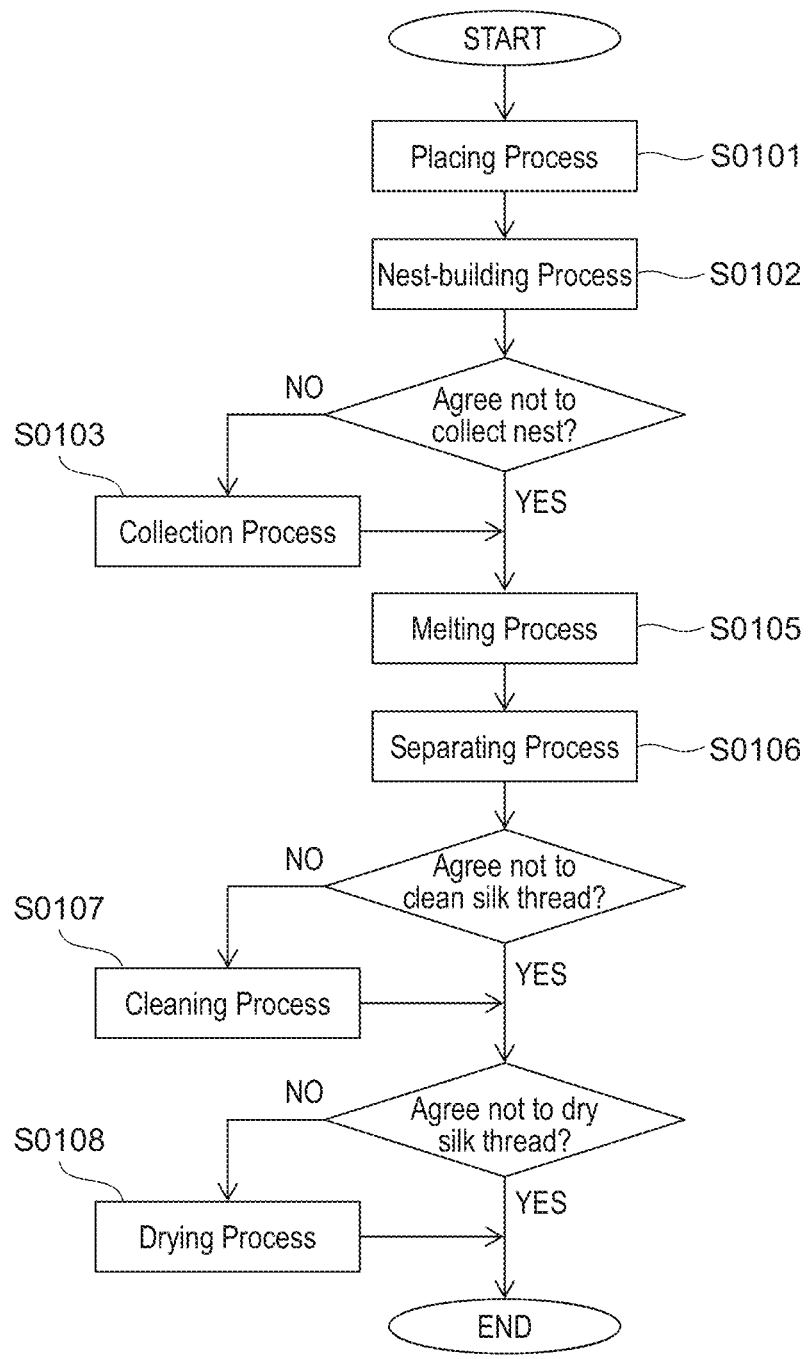
FIG. 1B shows a process flow diagram of a method of collecting a bagworm silk thread according to the present invention. This flow diagram shows a case in which the nest material to be used is a thermally meltable substance.

The first aspect of the present invention is a method of collecting bagworm silk threads. The process flow diagram of this aspect is shown in FIG. 1A and FIG. 1B. As shown in these figures, a method of collecting threads according to the present aspect is composed of two independent flows: the first flow (FIG. 1A) and the second flow (FIG. 1B).

2-1. Pre-treatment

Each flow will be specifically described below, and pre-treatment of a bagworm used in a method according to the present invention will first be described here.

In the present method, live bagworm is used in a placing process and a nest building process in both the first flow and the second flow. However, the bagworm is not fed, in principle, during these processes. This is because if dietary leaves are used as nest materials, it is possible that the purposes of the present invention cannot be achieved. Thus, it is preferable that the bagworm subjected to a method of collecting thread according to the present invention is sufficiently fed beforehand in the pre-treatment. The method and time for feeding are not limited. The bagworm may be supplied with a sufficient amount of food until they stop eating.

In addition, it is preferable to allow the bagworm to defecate after it is fed. This is for preventing the bagworm nests from getting dirty with feces. Leaving the bagworm at a usual rearing temperature for sufficient time for defecation after completion of feeding is enough for the defecation treatment. For example, the bagworm may be left at a temperature of 10 to 30° C., preferably 15 to 25° C. for, 30 minutes or more, 1 hour or more, 2 hours or more, 3 hours or more, 4 hours or more, 6 hours or more, 8 hours or more, 24 hours or less, 20 hours or less, 18 hours or less, 15 hours or less, 12 hours or less, or 10 hours or less.

Furthermore, naked bagworms are used in both the first flow and the second flow in the present method. Thus, bagworms and the bagworm nests need to be separated beforehand. In general, a bagworm hiding itself in a bagworm nest will never go out of the nest to expose its whole body throughout the whole larval stage. Therefore, a bagworm and/or a bagworm nest need to be subjected to some treatment to separate the bagworm and the bagworm nest.

The method of separating a bagworm and a bagworm nest is not limited. However, a naked bagworm subjected to the placing process has to build a nest in the subsequent nest building process. Thus, it is preferable to separate without causing any injury or excessive stress to the bagworm. For example, such method includes methods, in which a bagworm nest is cut open using a cutter such as scissors without damaging a bagworm in the nest or in which a bagworm is pushed out with pressure applied mildly from the outside of the nest. Alternatively, the method described in bagworm separation process described below may be used.

2-2. First Flow

The first flow (FIG. 1A) is characterized in that a solvent-soluble substance is used as a nest material. The present flow comprises a placing process (S0101), nest building process (S0102), dissolving process (S0104), and separation process (S0106) as essential processes and further comprises a collection process (S0103), washing process (S0107), and drying process (S0108) as optional processes. Each of the processes will be described below.

(1) Placing Process

The "placing process" (S0101) is a process of placing a naked bagworm separated from a bagworm nest in pre-treatment together with a solvent-soluble nest material. This process is an essential process in the present invention.

A nest material used in this process is not limited as long as the material is soluble in the specific solvent described above. Here, such nest material is classified into water-soluble nest material (water-soluble material) and low-polarity solvent-soluble nest material, and is specifically described below.

The term "water-soluble nest material" as used herein means a nest material composed of a substance that is soluble in water and is solid state under a dry environment. "Under a dry environment" refers to an environment under a normal state (at 15° C. to 25° C. under an atmospheric pressure condition) and humidity of 50% or less, preferably 40% or less, 30% or less, 20% or less, or 10% or less. Specific example of water-soluble nest material comprises gelatin, starch, pullulan, and the like. A water-soluble nest material used in this process may be, but not limited to, one nest material or a combination of two or more nest materials selected from the group mentioned above. The water-soluble nest material may be soluble not only in water (pure water) but also in an aqueous solution containing one solute or two or more solutes.

The term "low-polarity solvent-soluble nest material" as used herein means a nest material composed of a substance that is soluble in a low-polarity solvent and is solid state under the normal state described above. A "low-polarity solvent" as used herein corresponds mainly to a low-polarity organic solvent. Specific example thereof comprises hexane, toluene, chloroform, dichloromethane, dichloroethane, trichloroethylene, benzene, acetone, diethyl ether, xylene, methyl acetate, ethyl acetate, carbon tetrachloride, acetonitrile, and the like. For example, low-polarity solvent-soluble nest material comprises, but not limited to, polystyrene, vinyl acetate, cellulose acetate, acrylic resin, and polycarbonate. The material may be a combination of two or more low-polarity solvent-soluble nest materials as long as they are soluble in the same solvent.

The shape and size of a nest material used in this process is not limited. However, it is preferable that the nest material is processed into a suitable shape and size beforehand easier for a naked bagworm to handle for nest production so that the bagworm can use solvent-soluble nest materials to form a bagworm nest efficiently in a short time with the least possible stress. In a natural environment, pieces of leaves and small pieces of twigs of plants, particularly woody plants, are utilized as the nest material for the bagworm. Accordingly, the shape and size of a nest material in the present invention are preferably closer or similar to those of pieces of leaves and small pieces of twigs. For example, such a thin and small piece of shape as pieces of leaves have or a rod-like small piece of shape is suitable. Such a thin and small piece of shape may be structured or unstructured. For example, structured shape comprises a rectangular shape such as a strip or an approximate rectangular shape, or an oval shape or an approximate oval shape. The shape may be triangular or approximate triangular, polygonal of pentagonal or more, or approximate polygonal. The whole shape of the rod shape may be linear, branched, or tortuous, and the like, and is not limited to any of them. The cross-section of the rod-shaped material may be structured or unstructured. Examples of such structured shape comprises circular or approximate circular shapes, oval or approximate oval shape, triangular or approximate triangular shape, oval or approximate oval shapes, square or approximate square shape, rectangular or approximate rectangular shape, and polygonal of pentagonal or more or approximate polygonal shape. The suitable size of a nest material depends on the size of a bagworm to be used. In general, the size of a nest material used for a bagworm of larger species or last instar or penultimate instar bagworm is larger than that used for a bagworm of smaller species or young bagworm. Accordingly, the size of a nest material can be determined as appropriate according to the size of a bagworm to be used. The lower limit of the maximum length of a nest material is not limited, but it may usually be 0.2 times or more, 0.4 times or more, 0.5 times or more, 0.6 times or more, or 0.8 times or more larger than the body length of a bagworm to be used, and the upper limit may be 2.0 times or less, 1.8 times or less, 1.5 times or less, or 1.3 times or less larger than, or equal to or less than the body length. For example, if a *Eumeta japonica* last instar bagworm with a body length of 20 mm is used, the maximum length of a nest material is preferably 4 mm or more, 8 mm or more, 10 mm or more, 12 mm or more, or 16 mm or more, and 40 mm or less, 36 mm or less, 30 mm or less, 26 mm or less, or 20 mm or less.

In this process, plural nest materials processed into the shape and size described above are preferably used. In this case, the shape and size of the nest material to be used may be the same or different.

"Placing a bagworm together with a solvent-soluble nest material" refers to positioning both of them such that the naked bagworm can touch the solvent-soluble nest material and can easily obtain the nest material. This envisages, for example, that a naked bagworm is placed on or near a nest material spread in a predetermined place, that a naked bagworm is placed in a "predetermined place" and covered with a nest material, or a combination thereof. A "predetermined place" as used herein refers to a place for allowing a naked bagworm to produce a new bagworm nest using a solvent-soluble nest material. The place is not limited but is preferably a container or the like in that the prevention of an escape of a naked bagworm and the easiness of collecting a bagworm nest are considered. For example, a dish-shaped container such as a Petri dish or tray-shaped container is suitable.

Alternatively, a flat plate which comprises one recess that is containable a single naked bagworm or plural recesses, or a container which has them on the bottom may be used. This is not only because a naked bagworm can be retained in the recess but also because the stress of the bagworm can be reduced. A bagworm nest is usually formed in the recess. As a result, place where a bagworm nest is formed is identified beforehand and this improves the efficiency of bagworm nest collecting. The specific structure of the recess will be described in detail in the fifth aspect.

(2) Nest Building Process

The "nest building process" (S0102) is a process of allowing a naked bagworm to build a nest using the nest material and is an essential process in the present invention. The period of this process is not limited but is mainly from the time when a naked bagworm has started nest building to the time when the naked bagworm has completed nest building, in other words, correspond to the nest building period. A naked bagworm usually starts nest building immediately and spontaneously after the placing process. Thus, this process may be basically left to proceed during the nest building period. The nest building period varies depending on the species of a bagworm and the state of the individual, and is not to be limited in particular, but it may take 3 hours or more, 6 hours or more, 9 hours or more, 12 hours or more, 15 hours or more, 18 hours or more, 21 hours or more, or 24 hours or more, and 168 hours or less, 156 hours or less, 144 hours or less, 132 hours or less, 120 hours or less, 108 hours or less, 96 hours or less, 84 hours or less, 72 hours or less, 60 hours or less, 48 hours or less, 36 hours or less, or 30 hours or less after completion of the placing process.

It is recommended that the changes of temperature and humidity in the present process be none or a little so that a naked bagworm can complete nest building efficiently in a short time. It is preferable that the temperature is around 20° C., for example, ranges from 15° C. to 25° C., or from 18°

C. to 22° C., and that the humidity is around 50%, for example, ranges from 40% to 65%, or from 45% to 60%. There is no limit about light and dark period during this process, and it may have only a light period, or may have cyclical light and dark periods. For example, such cycle comprises a cycle having a 12-hour light period and a 12-hour dark period.

In this process, a dome-shaped bagworm nest is produced other than a spindle-shaped or a cylinder-shaped one. In general, a dome-shaped bagworm nest is more likely to be produced, if a plate used for nest building has light-blocking properties which do not allow light to penetrate from the lower face (bottom) and with a relatively short nest building time, for example, 1 hour or more, 3 hours or more, 5 hours or more, 8 hours or more, or 10 hours or more, and 50 hours or less, 48 hours or less, 44 hours or less, 40 hours or less, 36 hours or less, 32 hours or less, 28 hours or less, 24 hours or less, 20 hours or less, 16 hours or less, or 12 hours or less. On the contrary, a spindle-shaped or cylinder-shaped bag-like bagworm nest is more likely to be produced with a plate for nest building having a constitution to receive light radiated through the bottom of the plate or in cases where the longer nest building time even with the plate having light-blocking properties. For example, constitution that allow light to be radiated comprises a plate including a transparent material, a reflective material, or an artificial light source. In this way, regulating the constitution of a plate for nest building and the nest building time makes it possible to control the shape of a bagworm nest.

In the case of the silkworm, cocooning is carried out by continuous spinning, and a long fiber with a length of some hundred meters or more can thus be easily obtained by cocoon scouring and reeling. However, the bagworm pupates in its nest, and therefore do not perform cocooning. Additionally, since a nest of a bagworm is extended as the bagworm grows from the first instar, it is constituted with relatively fragmented old and new silk thread complicatedly entwined. Therefore, long fibers generally cannot be obtained from bagworm nests. However, in this process, it is possible to obtain bagworm silk threads that are longer and less entwined than usual bagworm nests. The term "long" refers to a length longer than the normal length in the art. Herein, the term "long" especially refers to being longer than the length of spun silk threads (a length of less than 1 m) obtainable from bagworms using conventional technology. Specifically, the term "long" refers to 2 m or more, preferably 3 m or more, more preferably 4 m or more, 5 m or more, 6 m or more, 7 m or more, 8 m or more, 9 m or more, or 10 m or more. The upper limit of the length is not particularly limited, but corresponds to the length of silk threads that bagworms can continuously spin in the method of the present invention, including, for example, 1.5 km or less, 1 km or less, 900 m or less, 800 m or less, 700 m or less, 600 m or less, 500 m or less, 400 m or less, 300 m or less, 200 m or less, or 100 m or less. The length of a spun fiber of bagworm silk threads is also the length of a monofiber constituting it, and corresponds to the length of the thread continuously spun by a bagworm.

(3) Collection Process

The "collection process" (S0103) is a process of collecting a produced bagworm nest and is an optional process in the present invention. This process comprises a nest material separation step and/or a bagworm separation step. Each of the steps will be described below.

(i) Nest Material Separation Step

The "nest material separation step" is a step of separating a bagworm nest and a residual nest material unused in nest production (hereinafter referred to as a "residual nest material"). After the nest building process, a newly produced bagworm nest, a bagworm (which may comprise a bagworm in the nest or a naked bagworm), and a residual nest material are in a mixed state. By separating and removing the residual nest material from them, the bagworm nest can easily be collected. This step is not necessarily a step to remove the bagworm, and thus, the bagworm nest and the bagworm may coexist after this step.

The method of separating a residual nest material is not limited. For example, the method comprises a method overturning a container used in the nest building process (an overturning method). The container may be moved forward and backward, right and left, or up and down, if necessary. If a nest material has been used for production of a bagworm nest, the bagworm silk thread is usually adhered to it. Thus, a nest material in a free state corresponds to a residual nest material. Additionally, the bagworm silk thread is often adhered to the container used in the nest building process with its bottom and the like, and inevitably, the bagworm nest is often adhered to the container. Accordingly, overturning the container to drop the nest material in a free state enables the residual nest material to be easily separated. Also, in this case, it is convenient that a naked bagworm unsuccessful in nest building and feces can be removed simultaneously. However, the bagworm nest may not be fixed to the container. In such cases, using a sieve to receive falling materials in addition to overturning the container enables the unfixed bagworm nest to be easily collected. The size of the sieve opening is not limited, as long as it is capable of separating a bagworm nest and a residual nest material by sieving. The opening is usually enough with 2 to 4 meshes. The sieve may be moved forward and backward, right and left, or up and down, if necessary. There is another method of blowing the nest building place with a blower or the like after the nest building process (a blowing off method). Since a nest material used in the present invention is light weighted, it is easy to separate by removing a residual nest material with air pressure blown with a blower and the like. Also, the overturning method described above and the blowing off method may be combined. A yet another method is the method of removing a residual nest material by suction (a vacuuming method). As mentioned above, since the bagworm nest is often fixed to a container used in the nest building process and the nest material used in the present invention is light weighted, only the residual nest material can be sucked regulating the suction force of a vacuum device. This makes it possible to separate the bagworm nest and the residual nest material. The vacuuming method may be carried out using a vacuum device having a mesh attached to the suction port thereof so as not to suck or remove a bagworm nest by mistake. In this case, the size of the mesh opening is enough with 2 to 4 mesh large.

(ii) Bagworm Separation Step

The "bagworm separation step" is a step of separating a bagworm nest and a bagworm. After the nest building process, the bagworm is in a newly produced bagworm nest except for the naked bagworm. In other words, by collecting the bagworm nest, the bagworm in the nest is concurrently collected. Here, it is possible to proceed with the subsequent dissolving process without removing the bagworm. However, there is a possibility that the bagworm silk thread is contaminated with the body fluid, feces, and the like of the bagworm during a solvent treatment. Accordingly, it is more preferable to separate the bagworm nest and the bagworm after the nest building process. The present step is a step to achieve this purpose and to collect only the bagworm nest.

The separation method in the present step is not limited. Any method for separating a bagworm nest and a bagworm can be utilized. For example, the method comprises a method in which a bagworm nest is cut open using scissors and the like to separate the bagworm nest and the bagworm in the nest as mentioned in pre-treatment described above. In view of the purposes of the invention, however, a preferable method in this step is to separate a bagworm nest and a bagworm without damaging the bagworm silk thread. For example, such method comprises a low oxygen method, a heating method, and combinations thereof.

(Low Oxygen Method)

The "low oxygen method" is method placing a bagworm with a bagworm nest under a low oxygen environment. The bagworm that has become hypoxic conditions in the nest spontaneously comes out of the nest seeking oxygen. The present method utilizes this feature of a bagworm.

The low oxygen environment may be a space in which low oxygen conditions can be maintained for a given period of time. For example, the environment comprises low oxygen conditions made in a predetermined space such as an airtight chamber or an airtight container (including a case and a bag). The low oxygen condition may be adjusted by an existing method for decreasing oxygen in a predetermined space. For example, the method comprises a deoxidation method, respiration consumption method, gas replacement method, combustion method, and combinations thereof.

The "deoxidation method" is a method of throwing deoxidant into an airtight space. It is convenient that the amount of oxygen in an airtight space can be adjusted by the amount of deoxidant thrown therein. For a deoxidant, a reducing agent or the like which absorbs oxygen through oxidation reaction is used. For example, reducing agent to be used comprises iron compounds such as iron powder and iron sulfide, and copper powder.

The "respiration consumption method" is a method of consuming oxygen in an airtight space by the biological respiration. The organism used for oxygen consumption is not limited to any species. It is convenient to use a microorganism that is not directly harmful to bagworms, such as a yeast or *E. coli*, but without using other organisms, encapsulating the bagworms to be separated at a relatively high density in an airtight space would also do.

The "gas replacement method" is a method of replacing gas in an air tight space with gas with a low concentration of oxygen. This method is advantageous in that a bagworm can be exposed to predetermined low oxygen conditions in a short time. Gas to be used for replacement (replacement gas) is preferably gas having the components closer to those of the air. For example, the gases comprise a mixture of nitrogen and oxygen. An oxygen concentration of the replacement gas may range from 0.5 to 15%, from 1 to 12%, from 2 to 10%, or from 4 to 8%. For example, in an airtight space having an exhaust port and a suction port with valves, gas replacement can be with opening both valves to receive replacement gas through the suction port and to exhaust the gas through the exhaust port from the container.

The "combustion method" is of consuming oxygen in an airtight container by combustion of a material.

In any of the methods, the oxygen concentration in the container is adjusted within the range of from 0.5 to 15%, from 1 to 12%, from 2 to 10%, or from 4 to 8%. Although the time for treatment under low oxygen conditions usually varies depending on the method, the conditions usually may be released when 50% or more, 60% or more, 70% or more, 80% or more, or 90% or more of the bagworm subjected to the low oxygen method come out of the nest.

The low oxygen method, with any of the methods mentioned above, is more effective with the bagworm nest treated with water beforehand. This is because permeation of water and formation of a water film deprive the bagworm nest of air permeability and thus, the inside of the nest becomes more hermetic and becomes oxygen-deficient faster. The method of treating a bagworm nest with water is not limited. For example, the method comprises a method immersing a bagworm nest in water, a method spraying a bagworm with water, and the like.

A bagworm separated from a bagworm nest by the low oxygen method can be transferred into gas with a usual concentration of oxygen, such as the air, to recover after being released from the low oxygen conditions, and then, can be reutilized for the present invention.

(Heating Method)

The "heating method" is a method of heating a bagworm with a bagworm nest from outside. If the temperature in the nest has become higher, the bagworm spontaneously comes out of the nest to avoid the heat. This method utilizes this feature of a bagworm.

The method to be used to heat a bagworm nest from outside may be an existing heating method and is not limited. For example, the method comprises a method of placing a bagworm nest on a heater or a hot plate, and a method of raising temperature in an airtight container. The heating temperature is a temperature that does not denature the bagworm silk thread and does not kill the bagworm in the nest. For example, the temperature may range from 35 to 60° C., from 38 to 55° C., from 40 to 50° C., or from 42 to 45° C.

A heating treatment in an airtight container is more effective with the container with high humidity inside. The humidity in the container may be adjusted within the range of from 70 to 100%, from 75 to 95%, from 80 to 90%, or from 85 to 88%. As with the low oxygen method, the bagworm nest may also be treated with water beforehand.

Using the low oxygen method, the heating method, or a combination thereof, the bagworm nest and the bagworm can be separated using a sieve and the like.

(4) Dissolving Process

The "dissolving process" (S0104) is a process of dissolving a nest material with a solvent. It is an essential process in the present invention. In this process, a nest material in a solid state is dissolved to turn into a liquid state.

A solvent to be used in this process is a solvent in which the nest material used in the nest building process can be dissolved. For example, if a water-soluble nest material is used in the nest building process, the solvent is water (pure water) or an aqueous solution containing one solute or two or more solutes. Alternatively, if a low-polarity solvent-soluble nest material is used in the nest building process, the solvent is a low-polarity solvent which can dissolve the nest material. For a specific example, if the low polarity solvent-soluble nest material is polystyrene or an acrylic resin, various kinds of low-polarity solvents such as hexane, xylene, chloroform, and carbon tetrachloride can be used as a solvent.

The temperature of a solvent to be used in this process is not particularly limited, as long as the temperature does not cause the bagworm silk threads to be damaged, denatured, or dissolved and is equal to or lower than the boiling point of the solvent. The temperature is usually in the range of room temperature, for example, from 1° C. to 35° C., from 5° C. to 32° C., from 10° C. to 30° C., from 12° C. to 27° C., from 15° C. to 25° C., or from 18° C. to 20° C. In general, however, a solute often dissolves more easily at a higher solvent temperature. In particular, a water-soluble nest material dissolves in a shorter time at a higher water temperature. Thus, the solvent temperature is preferably higher to dissolve the nest material rapidly. For example, if the solvent is water, the water temperature under the atmospheric pressure is preferably 35° C. or more, 38° C. or more, 40° C. or more, 42° C. or more, 45° C. or more, 48° C. or more, 50° C. or more, 52° C. or more, 55° C. or more, 58° C. or more, 60° C. or more, 62° C. or more, 65° C. or more, 68° C. or more, 70° C. or more, 72° C. or more, 75° C. or more, 78° C. or more, 80° C. or more, 82° C. or more, 85° C. or more, 88° C. or more, 90° C. or more, 92° C. or more, 95° C. or more, or 98° C. or more. Incidentally, the solvent can be heated before and/or during this process.

The method for dissolving a nest material is not limited to a particular method, as long as the bagworm nest can contact with the solvent. For example, the method comprises a method of immersing a bagworm nest into a solvent in a container, and a method of spraying or splashing a bagworm nest with a solvent. If a bagworm nest is immersed in a solvent, the solvent may be stirred.

The dissolving time is a time taken by the nest material to be completely dissolved in the solvent. A specific time can be determined as appropriate based on the property of the nest material and the type, temperature, and amount of the solvent. For example, if the nest material is polystyrene and is immersed and treated in a xylene or carbon tetrachloride solvent, at normal temperature, the lower limit may be 5 seconds or more, 10 seconds or more, 15 seconds or more, 20 seconds or more, 25 seconds or more, 30 seconds or more, 45 seconds or more, 50 seconds or more, or 60 seconds or more. Additionally, the upper limit may be 10 minutes or less, 8 minutes or less, 5 minutes or less, 3 minutes or less, or 2 minutes or less.

(5) Separating Process

The "separation process" (S0106) is a process of separating a dissolved nest material and bagworm silk threads. It is an essential process in the present invention. The method for separating bagworm silk threads and a solvent including a nest material after the dissolving process is not limited. Bagworm silk thread is a fibrous solid, but a solvent including a nest material is liquid, and thus, an existing method of separating solid and liquid can be utilized. For example, the separation can be carried out by centrifugation using a dehydrating device and the like. Bagworm itself and sometimes its feces remain as the solid form if the bagworm separation process in the collection process described above has not been carried out. In this case, for example, bagworm silk thread can simultaneously be separated from bagworm itself and the like and the solvent containing a nest material by entwining the bagworm silk thread around a rod and the like, but it is not limited to this method.

With this process, intended the bagworm silk thread can be obtained by separating a bagworm nest with the bagworm silk thread.

(6) Washing Process

The "Washing process" (S0107) is a process of washing the separated bagworm silk thread. This process is an optional process and may be carried out if necessary. In order to obtain purer bagworm silk thread, it is preferable to select the present process.

In some cases, the bagworm silk thread obtained from the separation process has some solvent or the like attached thereto. When the solvent evaporated, the nest material can solidify again which have been dissolved. Therefore, the solvent containing a nest material is completely removed by wash. By this process, it possible to simultaneously remove part of the feces or the like attached to the bagworm silk thread.

A washing solution to be used for wash may be a solvent used in the dissolving process. If a low-polarity solvent was used in the dissolving process, another solvent having high compatibility with the low-polarity solvent can be used as a washing solution. A washing solution having high volatility is preferable. In one example, if xylene is used as a solvent in the dissolving process, another low-polarity solvent such as toluene, benzene or a polarity solvent such as ethanol can be used as a washing solution. In this regard, a preferable washing solution to be used is a solvent containing no other component. If a water-soluble nest material is used, for example, pure water (including warm water) is more preferable as a washing solution than an aqueous solution containing any other solute.

The washing method is not limited, as long as the solvent used in the dissolving process can be removed from the bagworm silk threads. The bagworm silk threads may be sprayed with the washing solution or immersed in the washing solution. After the wash, the washing solution attached to the bagworm silk threads can be removed in the same manner as in the separation process.

The number of washes is not limited. The wash can be carried out once or plural times. The term "plural times" as used herein refers to, for example, 2 to 20 times, 2 to 15 times, 2 to 10 times, 2 to 7 times, 2 to 5 times, 2 to 4 times, or 2 to 3 times. In general, the wash is preferably carried out plural times. If the wash is carried out plural times, the washing solution to be used at each time may be the same or different. Also, the washing methods may be the same or different.

(7) Drying Process

The "drying process" (S0108) is a process of drying the bagworm silk thread. It is an optional process to be carried out, if necessary, in the present invention. On the surface of the bagworm silk thread obtained from the separation process or the washing process, some solvent or washing solution remains. This process is a process to remove the solvent or washing solution remaining on the bagworm silk thread after the separating process or the washing process by drying. After this process, intended bagworm silk thread can be obtained.

The drying method is not particularly limited, as long as the remaining solvent or washing solution can be reduced without denaturing or deteriorating the bagworm silk thread. For example, the method comprises a natural drying method (including sun drying) in which it is exposed to external air to vaporize the solvent or washing solution, an air drying method in which a blowing device or the like is used to blow them with warm air or cold air, a dehumidification drying method in which a dehumidifying agent is placed together in a hermetically sealed space for a given period of time, a heat drying method in which the solvent or washing solution is evaporated and dried by heating, a decompression drying method in which evaporation is carried out by degasification with a vacuum pump or the like in a container, or combinations thereof.

The drying time may be suitably determined depending on the solvent or washing solution used, the drying method used, and the like. For example, if a volatile solvent or washing solution such as xylene or ethanol is used and it is dried with an air drying method, drying time with 5 seconds to 10 minutes, 10 seconds to 5 minutes, or 20 seconds to 3 minutes is enough.

2-3. Second Flow

The second flow (FIG. 1B) is characterized in that a thermally meltable substance is used as a nest material. This flow comprises an placing process (S0101), nest building process (S0102), melting process (S0105), and separation process (S0106) as an essential process and a collection process (S0103), washing process (S0107), and drying process (S0108) as an optional process. Each of the processes will be described below.

(1) Placing Process

The placing process (S0101) in the second flow is basically the same as the placing process in the first flow. Accordingly, only the different points from the placing process in the first flow will be described below.

This process is different from the placing process in the first flow in that a thermally meltable nest material is used instead of a solvent-soluble nest material as a nest material.

The terms "thermally meltable (or thermally soluble)" as used herein refers to the property that readily melts by heat. The terms "thermally meltable nest material" refers to a nest material that is solid state at normal temperature (15° C. to 25° C.) under atmospheric pressure and melts and becomes liquid state by heat. The melting point of a thermally meltable nest material may be any temperature, as long as the temperature is lower than a temperature which causes the bagworm silk thread to be damaged, thermally denatured, or melted. Bagworm silk threads start thermally decomposing over 260° C., and thus, the melting point may be 260° C. or less at the highest. The melting point is preferably 200° C. or less, more preferably 150° C. or less, 140° C. or less, 130° C. or less, or 120° C. or less. To reduce the heating cost and not to expose the bagworm silk thread to high temperature more than necessary, the melting point is preferably a temperature which is higher than normal temperature and is 100° C. or less. For example, a suitable range is from 40° C. to 100° C., from 45° C. to 98° C., from 50° C. to 95° C., from 55° C. to 90° C., from 60° C. to 85° C., from 65° C. to 80° C., or from 70° C. to 75° C.

Specific examples of a component composing a thermally meltable nest material that can be used in the second flow comprises wax. The wax comprises plant-based waxes such as Japan wax and animal-based wax such as beeswax. The shape and size of the thermally meltable nest material are in accordance with that of the solvent-soluble nest material in the first flow.

(2) Nest Building Process

The "nest building process" (S0102) in the second flow is the same as the nest building process in the first flow except that a thermally meltable nest material is used as a nest material. Accordingly, this process may be carried out in accordance with the nest building process in the first flow.

(3) Collection Process

The "collection process" (S0103) in the second flow is the same as the collection process in the first flow. Accordingly, this process may be carried out in accordance with the collection process in the first flow.

(4) Melting Process

The "melting process" (S0105) is a process of melting a nest material by heating. It is a process characteristic of the second flow. In this process, a nest material in a solid state is melted to turn into a liquid state.

The heating temperature in this process is not particularly limited, as long as temperature is higher than the melting point of the thermally meltable nest material and does not cause the bagworm silk thread to be damaged, denatured, or dissolved. Since the melting point which is the lower limit of the heating temperature differs depending on the thermally meltable nest material, it may be determined appropriately according to the thermally meltable nest material used. Furthermore, since the bagworm silk thread do not thermally decompose at 260° C. or less, as described above, the upper limit of the heat temperature may be any temperature of 260° C. or less. However, because the possibility that bagworm silk threads exposed to a high temperature over 200° C. for a long time are damaged or denatured by heat cannot be eliminated, the upper limit of the heating temperature is preferably the melting point of the thermally meltable nest material used+50° C. or less, the melting point+45° C. or less, the melting point+40° C. or less, the melting point+35° C. or less, the melting point+30° C. or less, the melting point+25° C. or less, the melting point+20° C. or less, the melting point+15° C. or less, the melting point+10° C. or less, or the melting point+5° C. or less.

The method of melting a nest material is not particularly limited, as long as the bagworm nest and the like can be heated after the nest building process or the collection process. For example, the method comprises a method in which the bagworm nest and the like are placed on and heated with a heater or a hot plate, a method in which the bagworm nest and the like are placed in and heated with a microwave oven (a microwave), a method in which the bagworm nest and the like are exposed to hot air, a method in which the bagworm nest and the like are melted in a hot water bath in cases where the melting point of the thermally meltable nest material is lower than 100° C., and the like.

The melting time is a time taken by the nest material to be completely melted. A specific time can be appropriately determined based on the property of the nest material and the heating temperature. For example, if the nest material is beeswax having a melting point of 62° C., the melting time may be 30 minutes, 40 minutes, 50 minutes, 60 minutes, 70 minutes, 80 minutes, or 90 minutes under the heating temperature of 80° C.

(5) Separation Process

The "separation process" (S0106) is a process of separating the bagworm silk threads and the liquefied thermally meltable nest material. The separation process in the second flow basically has the same procedures as the separation process in the first flow. In the first flow, the bagworm silk thread and the solvent containing a solvent-soluble nest material are separated, and this process in the second flow is different in that a liquified thermally meltable nest material in place of the solvent to be separated. Bagworm silk thread is a fibrous solid, but the thermally meltable nest material in this process is in liquid state through the melting process, and thus, an existing method for separating solid from liquid can be utilized in accordance with the separating process in the first flow. However, if the temperature in this process becomes lower than the melting point of the thermally meltable nest material, it is possible that the thermally meltable nest material starts solidifying, and fails to be sufficiently separated. Thus, the thermally meltable nest material is treated so as not to solidify. For example, heating may be continued in this process at the comparable temperature as in the melting process, or a diluent to be used in the cleaning step described as follows may be added in this step to inhibit the solidification so that a liquid mixture of the thermally meltable nest material and the diluent can be formed and then separated.

(6) Washing Process

The "washing process" (S0107) is a process of washing the separated bagworm silk threads. The washing process in the second flow basically has the same procedure as the washing process. In the first flow, however, the bagworm silk thread obtained from the separation process have a solvent containing a solvent-soluble nest material attached thereto, and in the second flow, it is different in that the bagworm silk thread has a melted thermally meltable nest material attached thereto. Accordingly, only the points in which this washing process is different from the washing process in the first flow will be specifically described here.

In this process, if the temperature becomes lower than the melting point of the thermally meltable nest material, the attached nest material solidifies. Thus, the nest material is desirably removed completely by washing.

A washing solution to be used for wash is not particularly limited, as long as it does not cause bagworm silk threads to be damaged, denatured, or dissolved, and with a temperature higher than the melting point of the thermally meltable nest material used. For example, if the thermally meltable nest material is a beeswax having a melting point of 62° C., the beeswax attached to the bagworm silk thread can be melted and removed using water at 70° C. or more as a washing solution. A more preferable washing solution is a diluent having high compatibility with the thermally meltable nest material. In this case, the temperature of the diluent is not necessarily higher than the melting point of the thermally meltable nest material. The term "diluent" as used herein refers to a solvent in which the melted thermally meltable nest material can easily be dissolved. For example, using beeswax as a thermally meltable nest material, a diluent can be a solvent such as chloroform, carbon tetrachloride, and xylene.

(7) Drying Process

The "drying process" (S0108) in the second flow is the same as the drying process in the first flow. Accordingly, this process may be carried out in accordance with the drying process in the first flow.

2-4. Effect

It was not possible to obtain the bagworm silk thread without a stain from a bagworm nest collected in nature with conventional technologies. Additionally, the work efficiency had been extremely low, since contaminants such as twigs and leaves had to be manually removed over approximately one week to utilize bagworm nest. Further, even if a large amount of labor and time have taken, pigmentation and dirt were left on the bagworm silk thread. Therefore, only bagworm silk thread having low quality was obtained.

However, according to a method of collecting thread of the present invention, a large amount of pure bagworm silk thread comprising no contaminant can be collected from bagworm nest in a short time and in a convenient manner. Thus, bagworm silk thread lower in cost and higher in quality can be obtained than the bagworm silk thread obtained from a bagworm nest by conventional methods.

Furthermore, a bagworm used in the present invention can be reutilized, and one bagworm can be used to produce a bagworm nest plural times, and thus, compared with conventional methods, the amount of thread collected per bagworm can be increased.

3. Unwoven Fabric Constituted with Bagworm Silk Thread 3-1. Overview

The second aspect of the present invention is an unwoven fabric constituted with bagworm silk thread. An unwoven fabric according to the present invention is constituted with bagworm silk thread obtained from bagworm nest using the method of collecting according to the first aspect.

3-2. Constitution

Usually, bagworm silk thread obtained from one bagworm nest by the method of collecting according to the first aspect is often obtained in the form of a ball of thread entwined with one another as shown in FIG. 2h. An unwoven fabric according to the present invention is constituted with a material which is a ball of plural bagworm silk thread obtained from the method of collecting according to the first aspect. The unwoven fabric may contain a resin, another fiber component, and the like.

A method of forming a ball of bagworm silk thread into unwoven fabric can be carried out by an existing method of producing unwoven fabric. A ball of thread obtained from a method of collecting according to the first aspect is constituted with continuous long bagworm silk thread, and thus, the methods are not limited, but a spun lace method and a needle-punching method can be utilized.

4. Nest Material for Collecting Bagworm Silk Thread 4-1. Overview

The third aspect of the present invention is a nest material for collecting bagworm silk thread. This invention is a nest material essential for the method of collecting according to the first aspect. This is a nest material that is constituted with a solvent-soluble or thermally meltable material enabling the method of collecting according to the first aspect to be carried out and that has a shape and size prepared so that a naked bagworm can easily produce a new bagworm nest. Using a nest material according to the present invention allows the method of collecting to be carried out more easily.

4-2. Constitution

Nest material for collecting bagworm silk thread according to the present invention can be classified into solvent-soluble nest material and thermally meltable nest material as described on the method of collecting according to the first aspect. The constitution of each nest material will be described below.

(1) Solvent-soluble Nest Material

Solvent-soluble nest material can be subclassified further into water-soluble nest material and low-polarity solvent-soluble nest material. The component of each nest material is described in detail in the first aspect. Also, the shape and size of the solvent-soluble nest material are in accordance with the shape and size described in the first aspect. Accordingly, they are not specifically described here.

If nest material for collecting bagworm silk thread according to the present aspect is handled in bulk, the material can be a solvent-soluble nest material composed of plural components having plural shapes and/or sizes, provided that the constituents are soluble in the same solvent. Accordingly, they are not specifically described here.

(2) Thermally Meltable Nest Material

The component of the thermally meltable nest material is described in detail in the second aspect. Also, the shape and size of the thermally meltable nest material are in accordance with the shape and size described in the first aspect. Accordingly, they are not described here. If nest material for collecting bagworm silk thread according to the present aspect is handled in bulk, the materials can be thermally meltable nest material composed of plural components having plural shapes and/or sizes, provided that each of the materials has the comparable melting point.

4-3. Effect

A nest material for collecting a bagworm silk thread, such as a solvent-soluble nest material or a thermally meltable nest material, is essential for a method of collecting bagworm silk thread according to the first aspect. The component of each nest material is conventional component but it has not been processed into a shape or size that enables a bagworm to readily utilize as a nest material.

According to a nest material for collecting the bagworm silk thread according to this invention, it can be readily utilized, without being pre-processed, as a nest material to be used for a method of collecting the bagworm silk thread according to the first aspect.

5. Plate for Forming Bagworm Nest 5-1. Overview

The fourth aspect of the present invention is a plate for forming a bagworm nest. A plate for forming a bagworm nest according to the present invention is not limited, provided that the plate can be utilized for a method of collecting a bagworm silk thread described in the first aspect, that the plate enables a bagworm to produce a nest without causing excessive stress, and that the plate enables the produced bagworm nest to be efficiently collected.

5-2. Constitution

A plate for forming a bagworm nest according to the present invention is a plate including one or plural recesses. Each recess is formed to be containable a single bagworm.

The material of a plate according to the present invention is not particularly limited, provided that it can retain a given shape. For example, the material comprises plastic, metal, glass, synthetic rubber, ceramic, wood, reinforced paper, and combinations thereof. A material difficult to peel is preferable to avoid contamination caused by bringing in a part of the plate with in collecting a bagworm nest. Alternatively, the plate may be composed of a material which is the same or has the same properties as the nest material used, in order that any peeled part should cause no problem. The material is preferably light-blocking. It is usually in light-blocked state inside a bagworm nest, and thus, using a plate the recess of which is light-blocking can form an environment similar to the inside of the nest. In this case, since a bagworm forms a dome-shaped bagworm nest only over the open recess, it gives the bagworm few stress and burden.

Each recess preferably has a shape and size just enough to contain single naked bagworm. For example, the shape of the upper face of the recess as viewed from above preferably has an oval or approximate oval shape or a rectangular or approximate rectangular shape so as to contain an approximate spindle-shaped naked bagworm. In addition, the cross-sectional shape of the recess preferably has a semicircular or approximate semicircular shape or a square or approximate square shape so as to contain an approximate circular cross-sectional shaped naked bagworm. The size of the recess can be determined as appropriate according to the size of a naked bagworm to be contained. It is usual that the lower limit of the long axis of the upper face shape of the recess (wherein the long axis corresponds to the major axis in cases where the upper face shape is oval, or corresponds to the longer side in cases where the upper face shape is rectangular) may be 1.2 times or more, 1.4 times or more, or 1.5 times or more than the body length of a bagworm to be used, and that the upper limit may be 2.5 times or less, 2.2 times or less, 2.0 times or less, or 1.8 times or less than the body length. Additionally, the short axis of the upper face shape of the recess (wherein the short axis corresponds to the minor axis in cases where the upper face shape is oval, or corresponds to the shorter side in cases where the upper face shape is rectangular) may be 1.2 times or more, 1.5 times or more, or 1.8 times or more than the diameter of the maximum vertical section perpendicular to the long axis of a naked bagworm to be contained, and may be 2.5 times or less, 2.2 times or less, or 2.0 times or less than the diameter. Furthermore, the depth of the recess may be ⅓ or more, ½ or more, or ⅔ or more than diameter of the maximum vertical section perpendicular to the long axis of a naked bagworm to be contained, and may be 1.0 times or less, 1.2 times or less, 1.4 times or less, or 1.5 times or less than the diameter. For example, if a last instar bagworm of *Eumeta japonica* whose body length is 25 mm and a diameter of the maximum vertical section perpendicular to the long axis is 10 mm is used, the long axis of the upper face shape of the recess ranges from 30 mm to 62.5 mm, the short axis ranges from 12 mm to 25 mm, and the depth of the recess ranges from 3.3 mm to 15 mm.

Plural recesses can be placed in the plate. The constitution of the placement is not limited, but it is preferable that the space between the recesses is 5 mm or more, 8 mm or more, 10 mm or more, 12 mm or more, or 15 mm or more so that the naked bagworm to be contained in each recess do not interfere with one another.

A naked bagworm is contained in a recess, a nest material for collecting bagworm silk thread is scattered from above to cover the naked bagworm, and in this way, a dome-shaped bagworm nest is produced so as to cover the space above the recess with half of the body of the naked bagworm received in the recess. Under the dome-shaped bagworm nest, the under half space in which the bagworm is in contact with the plate has few or no bagworm silk thread spun therein, or has only a thin film composed of only bagworm silk thread containing no nest material. Thus, with just peeling the dome-shaped bagworm nest from the plate, the bagworm nest can be easily collected and additionally, it is easy to separate the bagworm nest with the bagworm. Further, with predetermining the position of a recess in the plate, it is possible to mechanize the collection of a bagworm nest since the position where a naked bagworm produces a bagworm nest can be preliminarily specified.

EXAMPLES

Example 1

Method (1) of Collecting Bagworm Silk Thread (Purpose)

A bagworm nest is produced by a naked bagworm using a low-polarity solvent-soluble nest material, further followed by collecting bagworm silk thread from the nest.

(Method and Result)

As the bagworm, the last instar larva of *Eumeta minuscula* collected at an orchard in Tsukuba, Ibaraki, Japan was used. A sufficient amount of a leaf of broadleaf tree was fed to the collected bagworm for three days. The bagworm was allowed to defecate under fasting state for one day, and then taken out of the bagworm nest using scissors.

Figure 2:
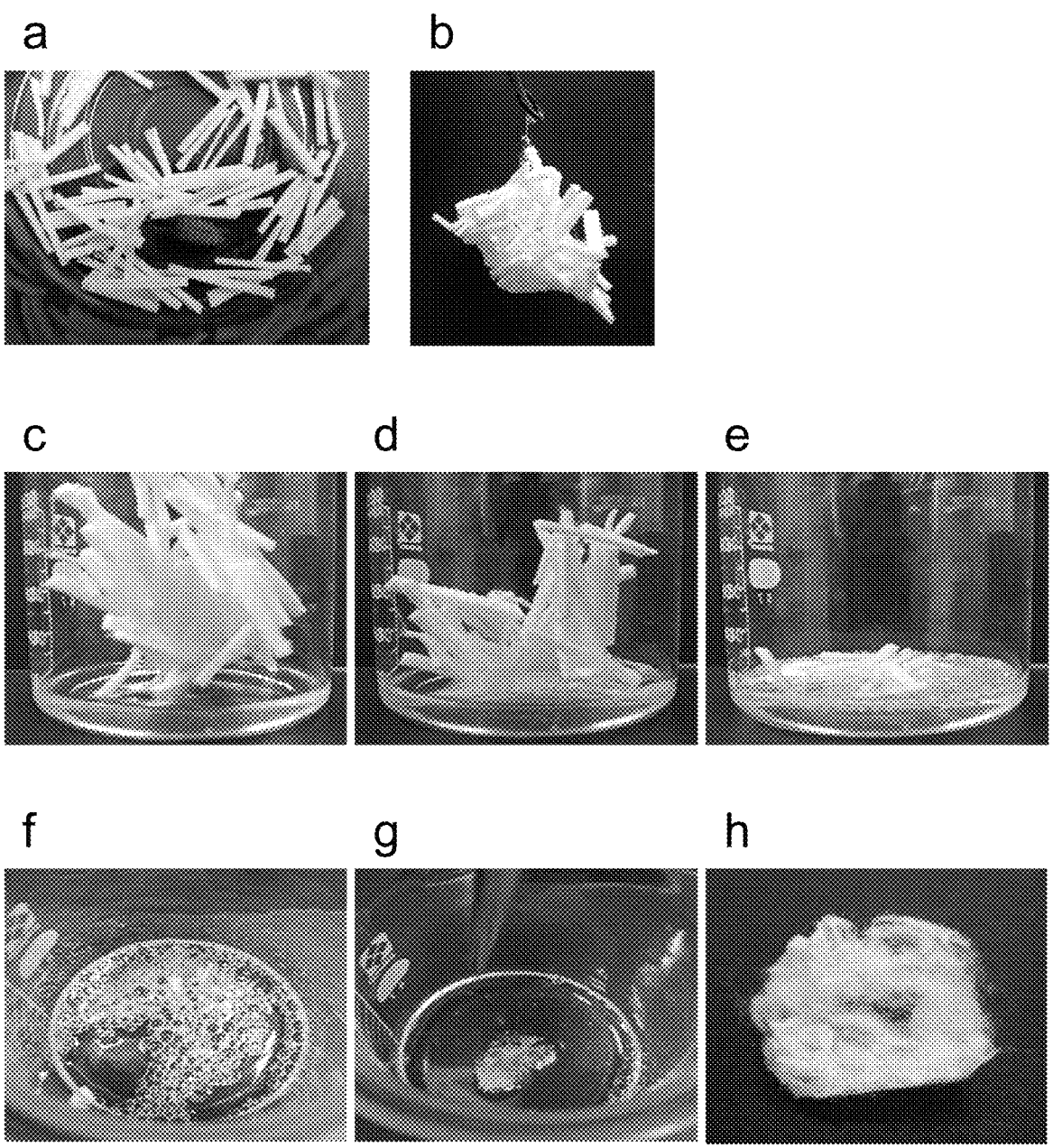
FIG. 2 shows the processes of a method of correcting a thread according to the present invention carried out in Example 1 in which styrene foams were used as a low-polarity solvent-soluble nest material. (a) shows an placing process in a method of collecting a thread according to the present invention. A naked bagworm (a last instar larva of *Eumeta minuscula*) was placed on thin pieces of styrene foam spread on the bottom of a beaker. (b) shows a bagworm nest collected after the four days of the nest building process, wherein the bagworm nest was produced using the thin pieces of styrene foam as a nest material. (c) to (g) show the change of the collected bagworm nest over time after it was cast into carbon tetrachloride used as a low-polarity solvent. The figure shows appearance, (c) at the time of casting into carbon tetrachloride, (d) 15 seconds after the casting, (e) 25 seconds after the casting, (f) 45 seconds after the casting, and (g) 60 seconds after the casting. Also, (h) shows the bagworm silk thread obtained according to the present invention.

FIG. 2 shows a method of collecting threads according to the present invention. On the bottom of a 100 mL glass beaker, thin pieces of styrene foam (polystyrene) prepared into 20 mm to 25 mm length of thin rods were spread as a low-polarity solvent-soluble nest material, then the beaker was placed in a transparent plastic case. The naked bagworm (a full length of 20 mm) taken out of the nest was placed on the thin pieces of styrene foam in the beaker, and left under the continuous lighting of a fluorescent lamp at atmospheric pressure at 25° C. for four days (a). After the four days, a bagworm nest (b) newly produced using the styrene foam as a nest material was collected. The bagworm nest had a longitudinal axis of 30 mm and a maximum transverse axis of 17 mm.

The bagworm nest from which the bagworm was removed was cast in a 100 mL glass beaker having carbon tetrachloride therein (c). After 15 seconds (d), 25 seconds (e), 45 seconds (f), and 60 seconds (g), the dissolving state of the thin pieces of styrene foam was observed. After the 60 seconds, the nest material of styrene foam was completely dissolved in the carbon tetrachloride.

The bagworm silk thread remaining in the carbon tetrachloride in the beaker was taken out 60 seconds after the start of dissolving, and washed with new carbon tetrachloride, then the bagworm silk thread was taken out. This process was repeated three times, and the finally obtained bagworm silk thread was naturally dried indoors for four days. As a result, the one process allowed obtaining 0.011 g of a bagworm silk thread from one bagworm nest, as shown in FIG. 2h. This bagworm silk thread comprised no contaminant at all and was completely without a stain.

Example 2

Method (2) of Collecting Bagworm Silk Thread (Purpose)

A bagworm nest is produced by a naked bagworm using a water-soluble nest material, further followed by collecting bagworm silk thread from the nest.
(Method and Result)

As the bagworm, similarly to Example 1, the last instar larva of *Eumeta japonica* collected at an orchard in Fuji, Shizuoka was used. The basic operation was carried out as in Example 1.

Figure 3:
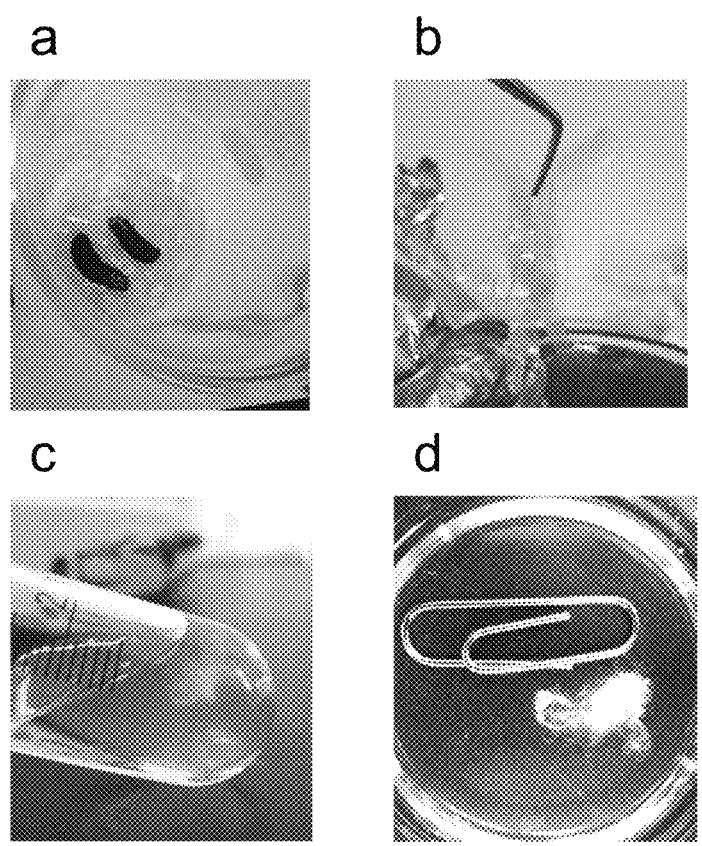
FIG. 3 shows the processes of a method of collecting a thread according to the present invention carried out in Example 2 in which small-piece capsules made of gelatin were used as a water-soluble nest material. (a) shows an placing process in a method of collecting threads according to the present invention. A naked bagworm (a last instar larva of *Eumeta japonica*) was placed on small pieces of hard capsule spread on the bottom of a beaker. (b) shows a bagworm nest collected after the three days of the nest building process, wherein the bagworm nest was produced using the small pieces of gelatin as a nest material. (c) shows the collected bagworm nest being washed with water at normal temperature after the bagworm nest was cast to water followed by heating them at about 60° C. for 20 minutes to completely dissolve the gelatin. Also, (d) shows the bagworm silk thread after the wash.

FIG. 3 shows a method of collecting according to the present invention. On the bottom of a 500 mL glass beaker, gelatin-made hard capsule (experimental gelatin capsule, TORPAC Inc.) shredded into 9 mm to 20 mm thin small pieces was spread as a water-soluble nest material. The naked bagworm (a full length of 20 mm) taken out of the nest was placed on the small pieces of gelatin in the beaker, and left at atmospheric pressure at 25° C. (a). After three days, a bagworm nest (b) newly produced using the small pieces of gelatin as a nest material was collected. The bagworm nest had a longitudinal axis of 60 mm and a maximum transverse axis of 16 mm.

About 100 mL of 60° C. warm water was added to a 300 mL glass beaker, and the beaker was swayed in a water bath of about 60° C. for five minutes. Then, the beaker was left to stand, and the warm water of the upper layer was removed by decantation. About 100 mL of 60° C. warm water was added to the residue, and treated in the same manner as above. This treatment was repeated further twice. With this operation, the nest material of small pieces of gelatin was completely dissolved, leaving the bagworm silk thread comprising the bagworm nest in the aqueous solution.

The bagworm silk thread remaining in the beaker was taken into a 10 mL test tube, and the bagworm silk thread was cleaned with 10 mL of normal temperature water (c), then the bagworm silk thread was taken out. This process was repeated three times, and the finally obtained bagworm silk thread (d) was dried with natural drying. As a result, the one process allowed obtaining 0.010 g of bagworm silk thread from one bagworm nest. As with Example 1, this bagworm silk thread comprised no contaminant at all and was completely without a stain.

Example 3

Method (3) of Collecting Bagworm Silk Thread (Purpose)

A bagworm nest is produced by a naked bagworm using a thermally meltable nest material, further followed by collecting bagworm silk thread from the nest.

(Method and Results)

As the bagworm, similarly to Example 1, the last instar larva of *Eumeta minuscula* collected at an orchard in Tsukuba, Ibaraki, Japan was used. The basic operation for preparing a naked bagworm was carried out as in Example 1.

Figure 4:
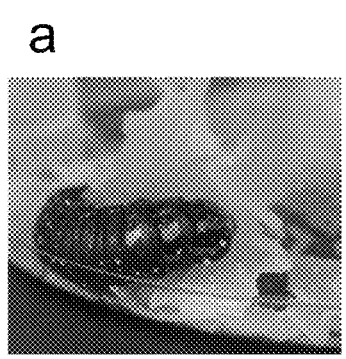
FIG. 4 shows the processes of a method of collecting threads according to the present invention carried out in Example 3 in which beeswax was used as a thermally meltable nest material. (a) shows an placing process in a process of collecting according to the present invention. A naked bagworm (a last instar larva of *Eumeta japonica*) was placed on small pieces of beeswax spread on the bottom of a beaker. (b) shows a bagworm nest collected after the five days of the nest building process, wherein the bagworm nest was produced using the small pieces of beeswax as a nest material. (c) shows the collected bagworm nest wrapped in a mesh. (d) shows the state of the bagworm nest described in (c), wherein the bagworm nest was cast to boiling water to melt the beeswax by boiling treatment. (e) shows the bagworm silk thread obtained by washing the resulting bagworm silk thread with xylene.
Figure 4:
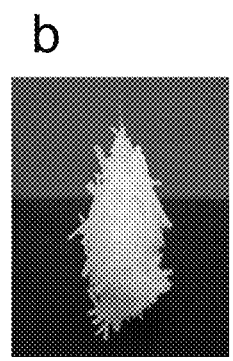
Figure 4:
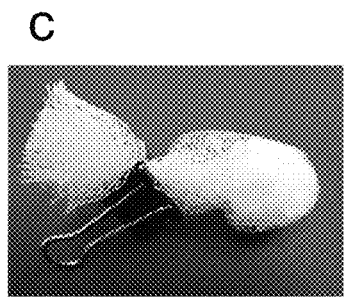
Figure 4:
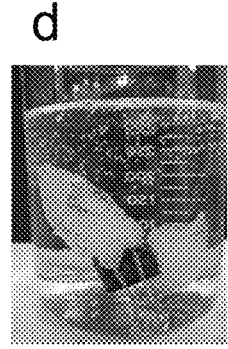
Figure 4:
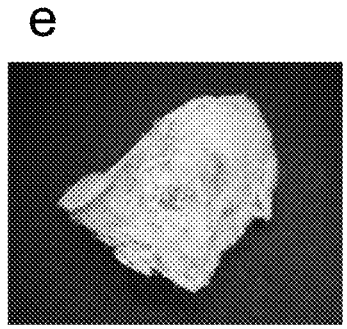

FIG. 4 shows a method of collecting according to the present invention. On the bottom of a 100 mL glass beaker, beeswax (manufactured by Yamada Bee Company, Inc.) prepared into 10 to 20 mm length of thin small pieces and 10 mm to 20 mm length of thin rods were spread as a thermally meltable nest material, then the beaker was placed on a transparent plastic case so that light could also come in through the bottom of the beaker. The naked bagworm (a full length of 25 mm) taken out of the nest was placed on the small pieces of beeswax in the beaker, and left under the continuous lighting of a fluorescent lamp at atmospheric pressure at 25° C. for five days (a). After the five days, a bagworm nest (b) newly produced using the beeswax as a nest material was collected. The bagworm nest had a longitudinal axis of 40 mm and a maximum transverse axis of 17 mm.

The bagworm nest from which the bagworm was removed was wrapped in a mesh (c), and was cast in boiling water (d). The boiling treatment was carried out for ten minutes, and the melting state of the beeswax was observed. After the ten minutes, the turbidity vanished and it became transparent state, and the beeswax was completely melted in the hot water.

Ten minutes after the start of casting in hot water, the bagworm silk thread remaining in the mesh was taken out and dried in the air. In the case where beeswax remained in the bagworm silk thread after the air drying, the beeswax was removed by wash with xylene. The one process allowed obtaining 0.008 g of bagworm silk thread as the finally obtained bagworm silk threads, as shown in FIG. 4e, from one bagworm nest. This bagworm silk thread also comprised no contaminant at all and was completely without a stain.

Example 4

Formation of Dome-Shaped Bagworm Nest (Purpose)

A dome-shaped bagworm nest is often produced in the nest building process in a method of collecting according to the present invention. In this Example, building of such a dome-shaped bagworm nest was examined.
(Method and Result)

As the bagworm, similarly to Example 1, the last instar larva of *Eumeta minuscula* collected at an orchard in Tsukuba, Ibaraki, Japan was used. The basic operation for preparing a naked bagworm was carried out as in Example 1.

To allow a bagworm to build a dome-shaped bagworm nest, a naked bagworm (a full length of 25 mm) taken out of a nest was placed in a stainless steel dish, and then, styrene foam prepared into 10 mm to 20 mm length of thin rods was spread around the naked bagworm. The bagworm was left with the continuously radiated light of a fluorescent lamp from above at atmospheric pressure at 25° C. for three days. After the three days, a dome-shaped bagworm nest was newly formed using styrene foam as a nest material.

Figure 5:
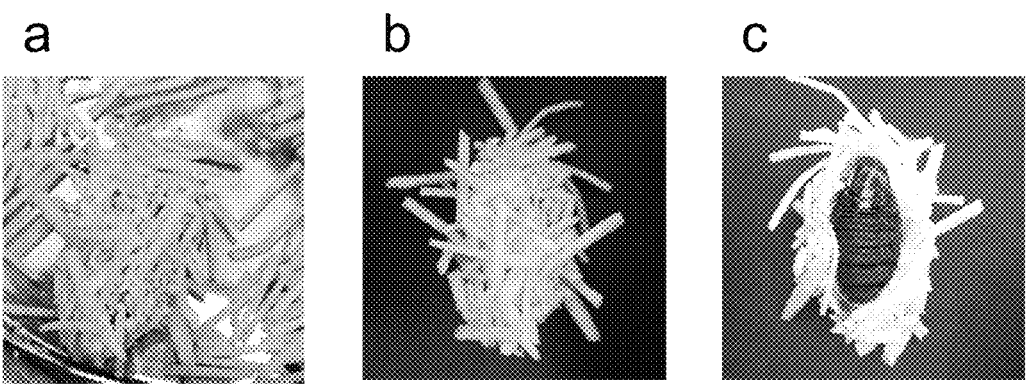
FIG. 5 shows a dome-shaped bagworm nest. (a) shows a dome-shaped bagworm nest formed on a stainless steel dish, wherein the picture was taken from above. (b) shows the dome-shaped bagworm nest peeled from the stainless steel dish and placed on a black sheet, wherein the picture was taken from above. (c) shows the dome-shaped bagworm nest as described in (b) turned upside down, wherein the picture was taken from above.

FIG. 5 shows a dome-shaped bagworm nest. (a) shows the dome-shaped bagworm nest formed on a stainless steel dish, wherein the picture was taken from above. Also, (b) and (c) show the dome-shaped bagworm nest taken out of the dish, wherein the pictures were taken from above and under respectively. A bagworm nest is usually bag-like, but this bagworm nest had nothing formed as the lower face in contact with the dish, and the bagworm nest was found to exhibit a half-spindle shape (a dome shape).

The dome-shaped bagworm nest had a longitudinal axis of 40 mm and a maximum transverse axis of 20 mm. It was verified that using a dish of a light-blocking material to block light from coming through the bottom thereof allows a bagworm to preferentially build the light-irradiated upper portion and side face of a nest, resulting in forming a dome-shaped bagworm nest.

All publications, patents, and patent applications cited herein should be incorporated herein by reference in their entirety.

What is claimed is:

1. A method of collecting a bagworm silk thread, comprising:
    placing process of placing a naked bagworm separated from a bagworm nest, together with a nest material(s) soluble in a solvent which does not damage, denature, or dissolve the bagworm silk thread;
    nest building process of allowing the naked bagworm to build a bagworm nest using the nest material(s);
    dissolving process of dissolving the nest material(s) in the solvent; and
    separation process of separating the dissolved nest material(s) from the bagworm silk thread.

2. The method according to claim 1, further comprising collection process of collecting the bagworm nest after the nest building process and before the dissolving process.

3. The method according to claim 1, wherein the solvent is water.

4. The method according to claim 1, wherein the solvent is a low-polarity solvent.

5. A method of collecting a bagworm silk thread, comprising:
    placing process of placing a naked bagworm separated from a bagworm nest, together with a thermally meltable nest material(s);
    nest building process of allowing the naked bagworm to build a bagworm nest using the nest material(s);
    melting process of melting the nest material under heating at a temperature which does not damage, thermally denature, or melt the bagworm silk thread; and
    separation process of separating the melted nest material(s) from the bagworm silk thread.

6. The method according to claim 5, further comprising collection process of collecting the bagworm nest after the nest building process and before the melting process.

7. The method according to claim 1, wherein the naked bagworm is placed in a recess of a plate in the placing process, the recess being containable the single naked bagworm body.

8. The method according to claim 7, wherein the plate is light-blocking.

9. The method according to claim 1, further comprising cleaning process of cleaning the separated bagworm silk thread.

10. The method according to claim 1, further comprising drying process of drying the bagworm silk thread.

11. An unwoven fabric formed of a bagworm silk thread(s) obtainable by using the method of collecting the bagworm silk thread according to claim 1.

* * * * *